US012618116B2

(12) United States Patent
Shi et al.

(10) Patent No.: US 12,618,116 B2
(45) Date of Patent: May 5, 2026

(54) SPECIFIC PRIMERS FOR IDENTIFYING ASIAN GYPSY MOTH AND METHOD OF DETECTION THEREBY

(71) Applicant: Beijing Forestry University, Beijing (CN)

(72) Inventors: Juan Shi, Beijing (CN); Wenzhuai Ji, Beijing (CN); Shuyue Liu, Beijing (CN)

(73) Assignee: Beijing Forestry University, Beijing (CN)

( * ) Notice: Subject to any disclaimer, the term of this patent is extended or adjusted under 35 U.S.C. 154(b) by 742 days.

(21) Appl. No.: 17/932,397

(22) Filed: Sep. 15, 2022

(65) Prior Publication Data

US 2023/0203598 A1 Jun. 29, 2023

(30) Foreign Application Priority Data

Dec. 24, 2021 (CN) .......................... 202111593718.2

(51) Int. Cl.
*C12Q 1/6888* (2018.01)
*C12Q 1/6844* (2018.01)

(52) U.S. Cl.
CPC ......... *C12Q 1/6888* (2013.01); *C12Q 1/6844* (2013.01)

(58) Field of Classification Search
CPC ............................ C12Q 1/6888; C12Q 1/6895
See application file for complete search history.

(56) References Cited

PUBLICATIONS

Wu et al (Ecology and Evolution, 2018, 8:2320-2325).*
Inoue et al. (Forest Ecology and Management, 2019, 434, 154-164).*

* cited by examiner

*Primary Examiner* — Sarae L Bausch
(74) *Attorney, Agent, or Firm* — Fitch, Even, Tabin & Flannery, LLP

(57) ABSTRACT

Disclosed is a pair of specific primers for identifying Asian gypsy moth and a method of detection thereby. In the present disclosure, based on the SS-COI technology, primers for distinguishing other species of *Lymantria* are designed according to the specific region of the mitochondrial COI gene of Asian gypsy moth. The pair of primers has accurate identification effects on different geographical populations, different insect states and different instars of Asian gypsy moth; in addition, the whole detection process only takes 2-3 hours, which has the advantages of rapidity and accuracy.

2 Claims, 7 Drawing Sheets

Specification includes a Sequence Listing.

SPECIFIC PRIMERS FOR IDENTIFYING ASIAN GYPSY MOTH AND METHOD OF DETECTION THEREBY

CROSS REFERENCE TO RELATED APPLICATION

This patent application claims the benefit and priority of Chinese Patent Application No. 202111593718.2, entitled "Specific primers for identifying Asian gypsy moth and method of detection thereby" filed on Dec. 24, 2021, the disclosure of which is incorporated by reference herein in its entirety as part of the present application.

INCORPORATION BY REFERENCE OF SEQUENCE LISTING

The xml file titled "HLP20220400312-Sequence_Listing" created Sep. 5, 2022 and being 8.27 KB in size, as filed with the present application via the USPTO patent electronic filing system, is incorporated by reference herein in its entirety as part of the present application. The xml file titled "HLP20220400312-Sequence Listing rev" created Oct. 21, 2022 and being 4.30 KB in size filed via the USPTO patent electronic filing system on Oct. 28, 2022 is incorporated by reference herein in its entirety as part of the present application.

TECHNICAL FIELD

The present disclosure relates to the field of forestry and plant quarantine, and in particular to specific primers for identifying Asian gypsy moth and a method of detection thereby.

BACKGROUND ART

The gyspy moth (spongy moth) *Lymantria dispar* Linnaeus is a widely distributed leaf-eating pest. According to the morphological characteristics, flight ability of females and geographical distribution, the latest subspecies classification research has divided them into three typical subspecies (Pogue& Schaefer, 2007): *Lymantria dispar dispar, Lymantria dispar asiatica* and *Lymantria dispar japonica*. The *Lymantria dispar dispar* is also known as European gypsy moth, *Lymantria dispar asiatica* and *Lymantria dispar japonica* are collectively referred to as Asian gypsy moth. Compared with the European gypsy moth, the female adult of the Asian gypsy moth has strong flight ability and its larvae have a wide range of hosts, with more than 500 kinds of forest trees serving as its host, while the female adult of the European gypsy moth has no flight ability and has about 250 species of larva hosts. Due to the migration distance of Asian female adults up to 25-40 miles and the characteristics of their wide host range, once introduced and established, Asian gypsy moth will speed much faster than European gypsy moth. Their harm to North America will be more serious than that of European gypsy moth. In order to prevent the introduction of Asian gypsy moth, the United States has successively imposed special quarantine measures to countries and regions where AGM is distributed. The establishment of quarantine measures has played an effective role in preventing the introduction of Asian gypsy moths. It can be seen that the Asian gypsy moth causes serious effects on the trade between countries, and also has a potential threat to the ecological environment. The destructive power and quarantine status of the Asian gypsy moth have greatly affected the phytosanitary and foreign friendly trade at important ports in China, which is the birthplace of the Asian gypsy moth. However, there are still several kinds of tussock moths, such as *Lymantria xylina, Lymantria apicebrunnea, Lymantria monacha* and *Lymantria mathura*. The morphology of their adults, larvae and even eggs is so similar to those of the *Lymantria dispar* that even the professional can also make false identifications. Because the species of *Lymantria* are mainly identified based on the morphology of lepidotic wing, and the moths found during the transportation of cargos are rarely with complete lepidotic wing pattern. In the process of port quarantine and cargo transportation, the traditional morphological methods can not meet the practical needs of rapid and accurate recognition and identification of *Lymantria dispar* and its related species. Therefore, it is very likely that other non-quarantine species of *Lymantria* will be identified as *Lymantria dispar* during quarantine, which may lead to the wrong direction for the establishment of quarantine measures. Therefore, rapid identification and accurate recognition of different species of *Lymantria* are of great significance for the implementation of control policies.

Given the quarantine significance of *Lymantria dispar* and the similar morphological characteristics of different species of *Lymantria*, in recent years, many studies have used molecular biology methods to develop rapid detection primers between Asian gypsy moth and European gypsy moth and other species of *Lymantria*, in which mitochondrial DNA has been proved to be a good target for rapid identification. Mitochondrial DNA (mtDNA) is characterized by simple structure, fast mutation rate (usually 5-10 times that of single-copy nuclear DNA), strong gene conservation, and matrilineal inheritance. It is called the second genetic information system of eukaryotic cells, or the extra-nuclear expression system. Compared with the nuclear genes, mtDNA can better reflect the evolutionary events in a short period of time, especially the evolution of low-order elements, and thus has been widely used for the identification of biological species and interspecific relations. At the same time, the widespread polymorphism of mtDNA in the same and different species, and in single or multiple populations of the same species also make it become an effective genetic marker for species identification.

At present, some studies have conducted the rapid identification of *Lymantria dispar* based on mitochondrial COI gene and 16S gene. However, on the one hand, most of the existing technologies are for the accurate identification of Asian gypsy moth and European gypsy moth, and few primers are designed for their related species. The number of samples collected by relevant studies on the detection of Asian gypsy moth and its relatives is insufficient to cover the different geographic populations in China. At present, studies have shown that different geographic populations of *Lymantria dispar* have differentiated in China, so primers that cover a small number of geographic populations in China are not representative. After tested, some primers are even positive to other insects species of *Lymantria* or negative to different geographical populations of *Lymantria dispar*. On the other hand, for the common related species of *Lymantria dispar*, such as *Lymantria umbrifera, Lymantria fumida* and *Lymantria* mathura, although previous studies on rapid identification have been done. *Lymantria apicebrunnea*, which severely occurred in parts of China in the past two years, is very similar to *Lymantria dispar*, and both of them are harmful together in the same area. Because of the outbreak only in recent years and few records of morphological identification, local prevention and control personnel could not distinguish them accurately, leading to a wrong identification and reporting. In addition, the morphology of eggs and larva stages of *Lymantria* are more difficult to distinguish than that of adult. When detecting the gypsy moth of different stages, the sensitivity of some primers cannot meet the requirements, and can only detect adults and larger larvae of body size. Therefore, a technique with wide coverage and high sensitivity is still not available in the rapid identification of Asian gypsy moth and its related species.

SUMMARY

An objective of the present disclosure is to provide a pair of specific primers for identifying Asian gypsy moth and a method of detection thereby.

To achieve the above objective, in a first aspect, the present disclosure provides a pair of specific primers for identifying Asian gypsy moth, including a forward primer set forth in SEQ ID NO:1 and a reverse primer set forth in SEQ ID NO:2. The amplified target segment is located at the 297th-647th bp of the mitochondrial COI gene of *Lymantria dispar*. The reference sequence number of the mitochondrial COI gene of *Lymantria dispar* on NCBI is KY923067.

In a second aspect, the present disclosure provides a detection reagent or a kit including the primers.

In a third aspect, the present disclosure provides a method for detecting Asian gypsy moth, comprising the following steps:

(1) extracting genomic DNA of an insect to be tested;

(2) performing PCR amplification using the primers set forth in SEQ ID NOs:1-2, with the genomic DNA as a template; and (3) analyzing amplified products.

The PCR reaction system is 25 µl, including 12.5 µl of 2×TaqPCR mix, 1-2 µl of 10 pmol/µl forward and reverse primers, 1-3 µl of DNA template, and a balance of ddH$_2$O to 25 µl.

The PCR reaction program includes: an initial denaturation at 94° C. for 3 minutes; followed by 30 cycles of denaturation at 94° C. for 30 seconds, annealing at 49° C. to 56° C. (preferably 50° C.) for 30 seconds and extension at 72° C. for 1 minute; and a final extension at 72° C. for 5 minutes.

In the aforementioned method, step (3) includes the following steps: detecting the amplified products by agarose gel electrophoresis, and if a characteristic band of 350 bp appears, it is determined that the insect to be detected is Asian gypsy moth.

According to the technical scheme, the embodiments of present disclosure at least has the following advantages and beneficial effects:

In the present disclosure, based on the SS-COI technology, primers for distinguishing other species of *Lymantria* are designed according to the specific region of the mitochondrial COI gene of Asian gypsy moth, and the pair of primers has accurate identification effects on different geographical populations and different instars of Asian gypsy moth; in addition, the whole detection process only takes 2-3 hours, and the detection sensitivity is that *Lymantria dispar*: related species=1:100 (DNA molar ratio), which has the advantages of rapidity and accuracy. It may be used for rapid detection and identification of plant quarantine in customs.

BRIEF DESCRIPTION OF THE DRAWINGS

FIG. 3A: 1, 2, 3, 4, and 5 represent *Lymantria dispar asiatica, Lymantria xylina, Lymantria monacha, Lymantria apicebrunnea,* and sterile deionized water, respectively. The four groups refer to different annealing temperatures, which are 56° C., 55° C., 54° C., and 53° C. in sequence.

FIG. 3B: 1, 2, 3, and 4 represent *Lymantria dispar asiatica, Lymantria xylina, Lymantria monacha, Lymantria apicebrunnea* and sterile deionized water, respectively. The four groups refer to different annealing temperatures, which are 52° C., 51° C., 50° C. and 49° C. in sequence.

DETAILED DESCRIPTION OF THE EMBODIMENTS

Figure 1:
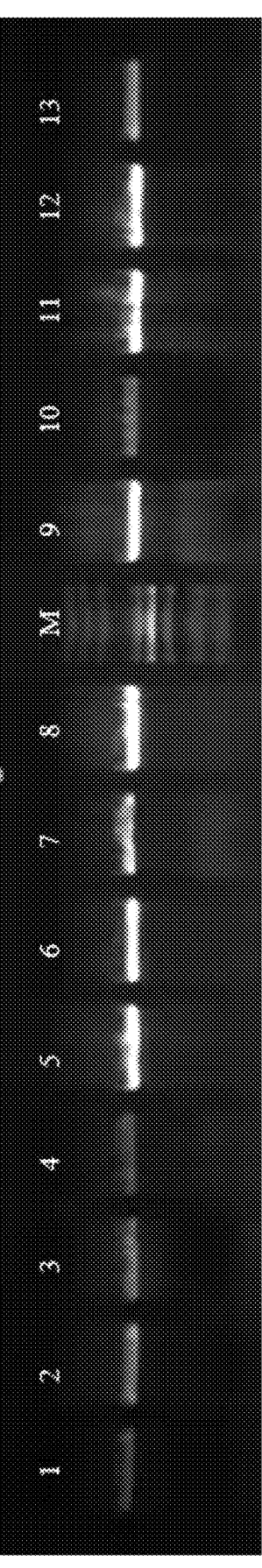
FIG. 1 is an electrophoretogram showing the amplification of COI genes of four species of the *Lymantria* by using universal primers (C1-J1709, C1-N2776) in a preferred example of the present disclosure, wherein 1-2 refer to *Lymantria apicebrunnea;* 3-5 refer to *Lymantria monacha* and 6-8 refer to *Lymantria xylina;* 9-13 refer to Asian gypsy moth, and M refers to DNA marker.

A detection method for rapidly identifying Asian gypsy moth and its related species is established by means of molecular biological means in the present disclosure. The method is not limited by stadium, development states and geographical populations, optimizes the rapid identification primers and the amplification system greatly for *Lymantria*

*dispar* and the related species, and provides a powerful tool for quarantine pest identification and phytosanitary work Firstly, mitochondrial COI fragments of Asian gypsy moth and its related species are amplified by using a general primer pair which is suitable for lepidoptera and through sequence alignment and correction. The upstream primer is 5'-AATTGGWGGWTTYGGAAAYTG-3' (SEQ ID NO:3), and the downstream primer is 5'-GGTAATCAGAGTATCGWCGNGG-3' (SEQ ID NO:4). For the purpose of better amplification, the primers are degenerate primers, in which W is A or T, Y is C or T, and N is A, T, G or C.

Furthermore, the sequencing results of the same COI fragments of the 4 species of *Lymantria* are subjected to sequence alignment by using Bioedit software. The fragments, which are conservative within the Asian gypsy moth but significantly different among species, are identified and used for designing specific primers, in which intraspecific conservation is used for ensuring that the designed primers are able to identify different individuals of Asian gypsy moth, and interspecific differences are used for ensuring that the designed primers have enough specificity to detect Asian gypsy moth. In the present disclosure, Primer 5.0 is used to design a pair of specific primers for Asian gypsy moth, namely, AGM(F) and AGM(R). The primer sequences are as follows (SEQ ID NOs:1-2):

```
                                         (SEQ ID NO: 1)
  AGM(F): 5'-CCTTCTACTTTTATCTTTACCTGTT-3'

(SEQ ID NO: 2)
  AGM(R): 5'-ATTGTAGCAGAGGTAAAG-3'
```

The present disclosure provides a method for detecting Asian gypsy moth by using the above-mentioned primers, which includes the following steps: extracting the DNA template of the sample to be detected, adding primers for PCR amplification, and performing agarose gel electrophoresis on an amplified product; if the fragment size of a band generated by electrophoresis is about 350 bp, the sample is determined to be Asian gypsy moth.

The present disclosure provides a PCR reaction system for detecting Asian gypsy moth by using the primers, and the PCR reaction system includes 12.5 µl of 2×TaqPCR mix, 1 µl of 10 pmol/µl forward and reverse primers, 1 µl of DNA template, and 9 µl of sterile distilled water. The PCR reaction program includes: pre-denaturation at 94° C. for 3 minutes; 30 cycles of denaturation at 94° C. for 30 seconds, annealing at 50° C. for 30 seconds and extension at 72° C. for 1 minute; and a final extension at 72° C. for 5 minutes, the resulting products are stored at 4° C.

The present disclosure provides a kit for detecting Asian gypsy moth, including the above-mentioned primers and a corresponding DNA extraction reagent, and TaqPCR mix.

Specifically, the method for detecting Asian gypsy moth is as follows:

1) Extraction of genomic DNA of the insects to be tested
2) Amplification of target fragments using SS-COI primers: the amplification is performed by the above-mentioned PCR reaction system and PCR reaction program, using genomic DNA of the insect to be detected as a template; the amplified products are stored at 4° C.
3) agarose gel electrophoresis: 5 µl of the amplified stock solution is pipetted for electrophoresis in 1.5% agarose gel at 110V for 25-30 minutes. A nontoxic gelred is used as nucleic acid dye, and 1×TAE buffer is used as electrophoresis buffer. DL2000 DNA Marker is added as a marker during electrophoresis, and after electrophoresis, an Omega LumG gel imager is used to observe if any bands appeared. If the fragment size of a band is about 350 bp, the sample to be tested is identified as Asian gypsy moth. The following examples are intended to illustrate the present disclosure, but not to limit the scope of the present disclosure. Unless otherwise specified, the examples are carried out according to conventional experimental conditions, such as "Molecular Cloning: A Laboratory Manual" by Sambrook et al. (Sambrook J & Russell D W, 2001), or according to conditions suggested by the manufacturer's instructions.

Example 1. Method for Detecting Asian Gypsy Moth

1. Extraction of Insect Genomic DNA

Genomic DNA of Asian gyspy moth and its related species collected from different regions in China was extracted using an OMEGA genomic DNA mini-kit.

(1) No more than 50 mg of insect tissue (thorax or leg) was grinded in liquid nitrogen with a mortar and pestle, and the powder was transferred to a clean 1.5 mL microcentrifuge tube.

(2) 350 µl of Buffer CTL and 25 µl of Proteinase K were added, and the resulting mixture was vortex mixed and incubated at 60° C. for 30 min until the insect tissue powder was completely dissolved.

(3) 350 µl of chloroform:isoamyl alcohol (24:1, v/v) mixture was added, and vortex mixed, followed by centrifugation at 10,000 g for 5 min at room temperature, and the supernatant was carefully transferred to a new 1.5 mL centrifuge tube.

(4) An equal volume of Buffer CBL was added, vortex mixed at maximum speed for 15 s, and incubated at 60° C. for 10 min.

(5) Equal volume of absolute ethanol was added and the mixture was vortex mixed at maximum speed for 15 s.

(6) HiBind® DNA column was inserted into a 2 mL collection tube, 750 µl of the mixture solution from step (5) was added, followed by centrifugation at 10,000 g for 1 min at room temperature, and the resulting filtrate was discarded.

(7) HiBind® DNA column was inserted back into the 2 mL collection tube, 500 µl of Buffer HB was added, followed by centrifugation at 10,000 g for 1 min, and the resulting filtrate was discarded.

(8) HiBind® DNA column was inserted into a new 2 mL collection tube, 700 µl of DNA WashBuffer was added, followed by centrifugation centrifuge at 10,000 g for 1 min, the resulting filtrate was discarded, and the operation was repeated once.

(9) HiBind® DNA column was inserted back into the 2 mL collection tube and the empty column was centrifuged at 10,000 g for 2 min at room temperature for drying.

(10) HiBind® DNA column was inserted into a new 1.5 mL centrifuge tube, 50-100 µl of Elution Buffer preheated at 60° C. was added, and the obtained product was allowed to stand for 2 min at room temperature and then centrifuged at 10,000 g for 1 min to elute the DNA.

(11) DNA concentration detection. The concentration of the extracted DNA was detected by an ultramicrospectrophotometer. Before detection, the detection wells were firstly washed with deionized water, and after drying, 1 μl of Elution Buffer used for DNA extraction was pipetted for correction. After the correction, 1 μl of sample was pipetted and loaded into the detection wells, and the concentrations of DNA were measured separately.

During the process of DNA extraction, by addition of chloroform:isoamyl alcohol in the volume ratio of 24:1, the protein was denatured more effectively and the impurity pollution was reduced. At the same time, the foam produced by lysis solution and loss of DNA could also be reduced.

2. Amplification of Target Genes of Asian Gypsy Moth and its Related Species

The COI gene in the mitochondrial DNA genome was selected for the design of specific primers, and a pair of universal primers suitable for the mitochondrial corrected COI gene of *Bombyx mori* were used to synthesize degenerate primers for the amplification of mitochondrial COI genes in four species of *Lymantria dispar, Lymantria xylina, Lymantria apicebrunnea* and *Lymantria monacha* through sequence alignment. The universal primer sequences are as follows:

```
                                    (SEQ ID NO: 3)
C1-J1709: 5'-AATTGGWGGWTTYGGAAAYTG-3'

(SEQ ID NO: 4)
C1-N2776: 5'-GGTAATCAGAGTATCGWCGNGG-3'
``` in which, W is A or T, Y is C or T, and N is A, T, G or C.

The target segments amplified by the degenerate primers C1-J1709 and C1-N2776 were located at the 248-1295 bp of Asian gypsy moth mitochondrial COI gene.

The total system of PCR reaction was 25 μl, including 12.5 μl of 2×TaqPCR mix (Beijing Zhongke Yuboiolab Biotechnology Co., Ltd.), 1 μl of 10 pmol/μl forward primer and reverse primer, 1 μl of DNA template, and a balance of sterile distilled water to 25 μl. Reaction conditions included the following: pre-denaturation at 94° C. for 3 minutes; 30 cycles of denaturation at 94° C. for 30 second, annealing at 55° C. for 30 second and extension at 72° C. for 1 minute; and a final extension at 72° C. for 5 minutes; the products were stored at 4° C. The PCR products (5 μl) were then analyzed and detected in 1.5% agarose gel electrophoresis. Non-toxic gelred dye was added during the preparation of agarose gel, and the fragment size was marked with DL2000 DNA marker. The samples with bands were sent to Beijing Tsingke Biotechnology Co., Ltd. for bidirectional sequencing. The amplification result are shown in FIG. 1.

3. Design of SS-COI Primers for Asian Gypsy Moth

After the COI gene of individuals of different geographical populations of Asian gypsy moth was amplified, intraspecific sequence alignment of Asian gypsy moth was carried out firstly to find the intraspecific conservative fragments of Asian gypsy moth, and then the alignment between the COI gene of Asian gypsy moth and those of other related species was carried out to find the fragments with high mutation rate of Asian gypsy moth relative to the related species. Finally, in combination with the intraspecific conservative fragments, the fragments which were conservative within the Asian gypsy moth species but significantly different among species were selected for specific primer design, Bioedit software was used for sequence alignment. In this study, a pair of specific primers: AGM(F), AGM(R) were designed by using Primer 5.0. The primer sequences were as follows (SEQ ID NOs:1-2):

8

```
                                    (SEQ ID NO: 1)
AGM(F): 5'-CCTTCTACTTTTATCTTTACCTGTT-3'

(SEQ ID NO: 2)
AGM(R): 5'-ATTGTAGCAGAGGTAAAG-3'
```

Figure 2:
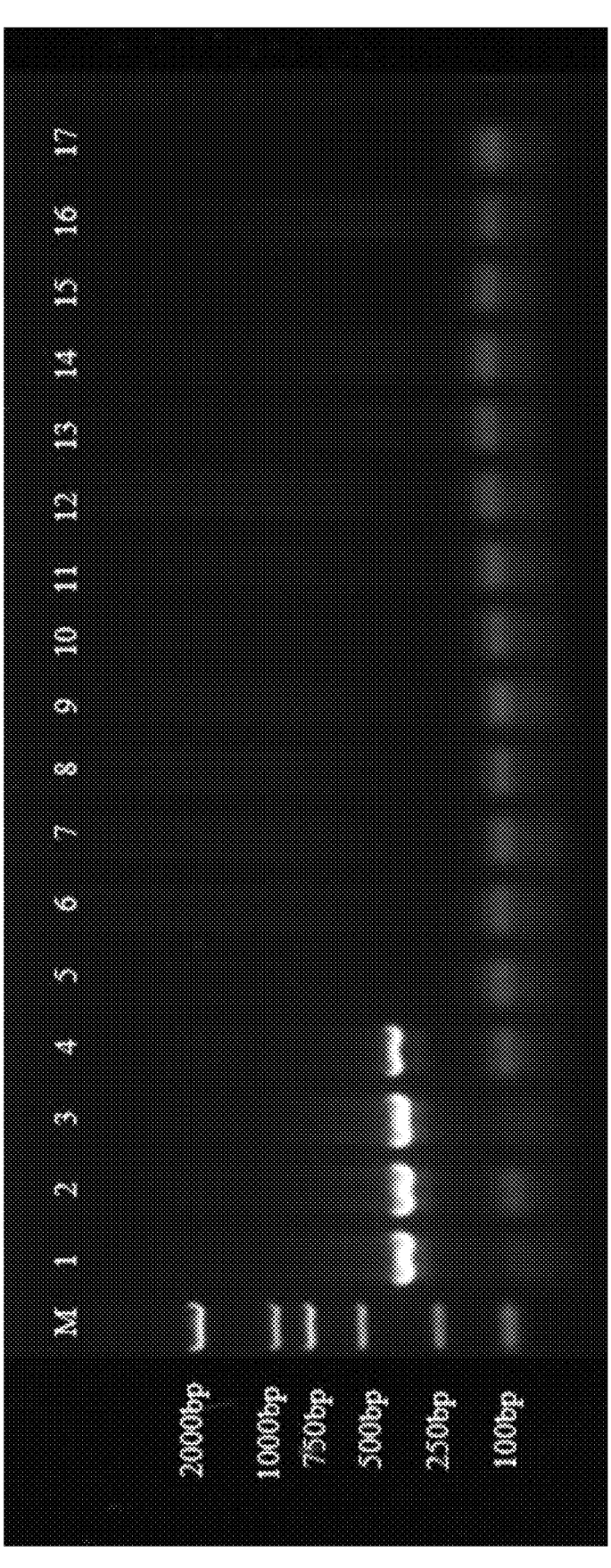
FIG. 2 is an electrophoretogram of the amplification of Asian gypsy moth and its related species, *Lymantria xylina, Lymantria monacha,* and *Lymantria apicebrunnea* by using specific primers AGM(F) and AGM(R) in a preferred example of the present disclosure. Wherein, M::DL 2000 DNA marker (2000, 1000, 750, 500, 250, 100 bp respectively from top to bottom); lanes 1-4 refer to Asian gypsy moth (where 1 and 2 refer to *Lymantria dispar asiatica* of Asian gypsy moth; 3 and 4 refer to *Lymantria dispar japonica* of Asian gypsy moth); 5-8 refer to *Lymantria xylina;* 9-12 refer to *Lymantria monacha;* 13-16 refer to *Lymantria apicebrunnea;* 17 refers to sterile deionized water.

4. Specificity Test of SS-COI Primers of Asian Gypsy Moth (1) The related species of *Lymantria dispar:Lymantria xylina, Lymantria monacha* and *Lymantria apicebrunnea* were used as negative controls and water was used as blank control to carry out specificity tests of primers, and four samples were selected from each species for the test. The PCR reaction system was 25 μl, including 12.5 μl of 2×TaqPCR mix (Beijing Zhongke Yuboiolab Biotechnology Co., Ltd.), 1 μl of 10 pmol/μl of forward and reverse primers, 1 μl of DNA template, and a balance of sterile distilled water to 25 μl. The reaction procedure included: pre-denaturation at 94° C. for 3 minutes; 30 cycles of denaturation at 94° C. for 30 seconds, annealing at 55° C. for 30 seconds and extension at 72° C. for 1 minute; and a final extension at 72° C. for 5 minutes; it was showed that only the sample of Asian gypsy moth were amplified with bright bands (FIG. 2), while no band appeared for the negative and blank controls.

Figure 3A:
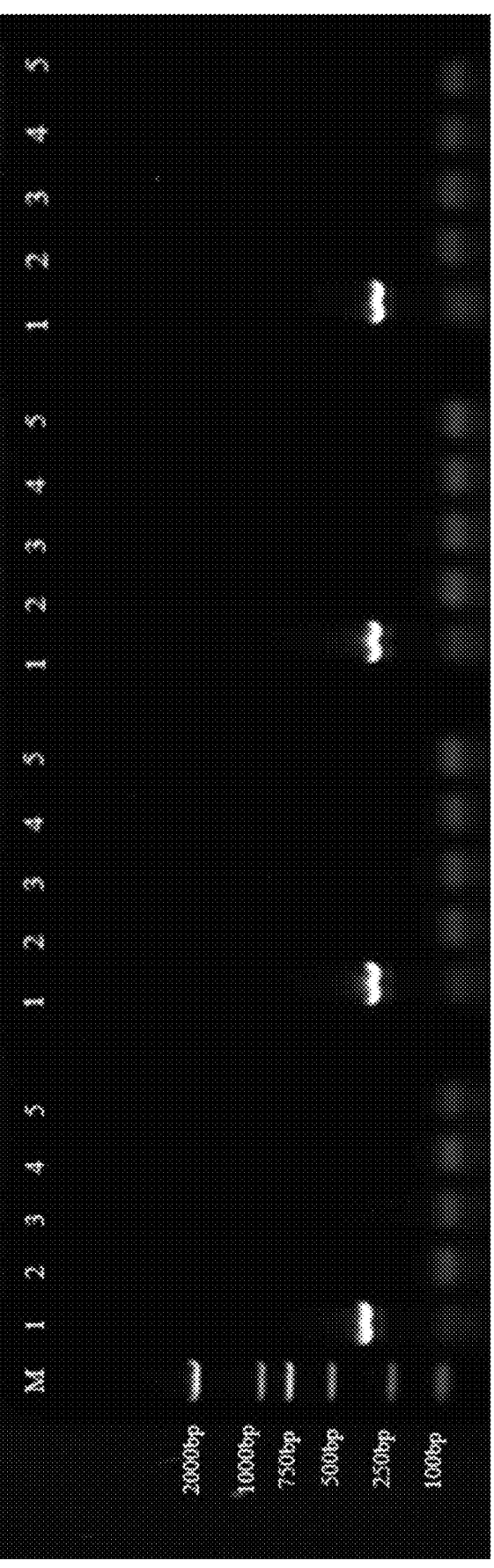
FIGS. 3A and 3B are electrophoretograms showing the optimum annealing temperatures for detecting the primers AGM(F) and AGM(R) by setting 8 temperature gradients from 49° C. to 56° C. in a preferred example of the present disclosure, in which, M refers to DL2000 DNA marker.
Figure 3B:
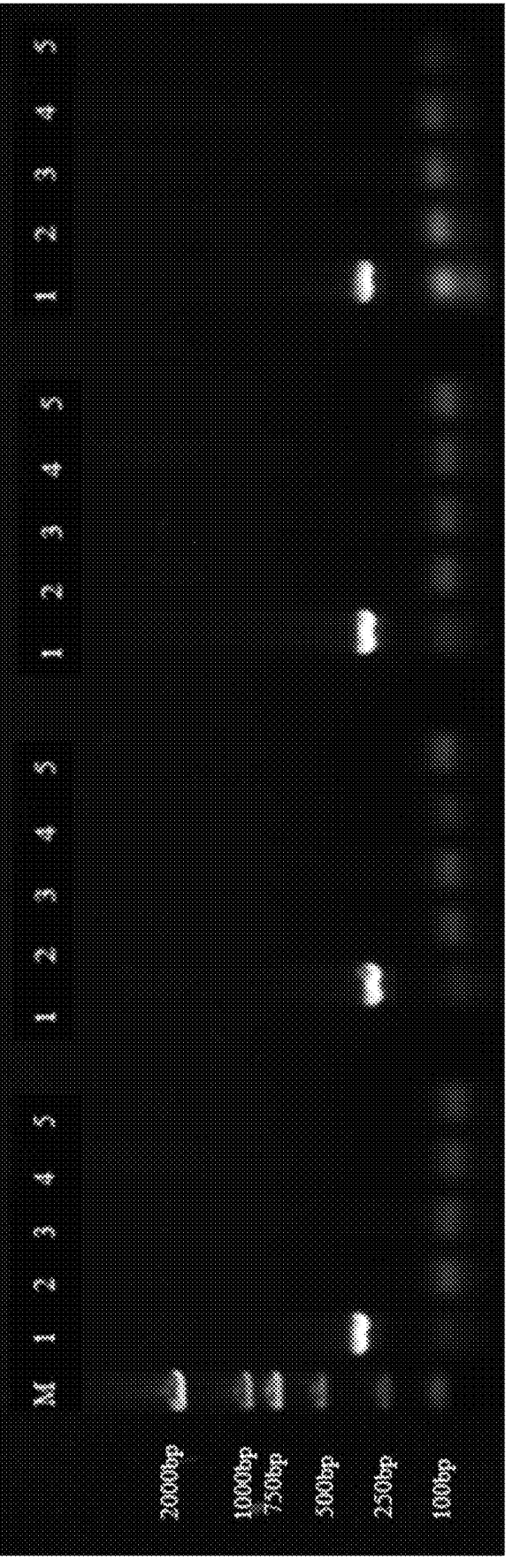

(2) Eight annealing temperatures (49° C.-56° C.) were set for temperature gradient PCR to explore the optimal annealing temperature. According to electrophoresis results, it was showed that there was a wide range of annealing temperature for the specific primer pairs for Asian gypsy moth designed by the present disclosure, and only the sample of Asian gypsy moth showed target bands from 49° C. to 56° C. (FIG. 3A and FIG. 3B), indicating that the stability and specificity of the pair of primers were good, the pair of primers had amplification effects on samples at a plurality of annealing temperatures, thereby excluding inaccuracy caused by temperature differences of different PCR instruments.

Figure 4:
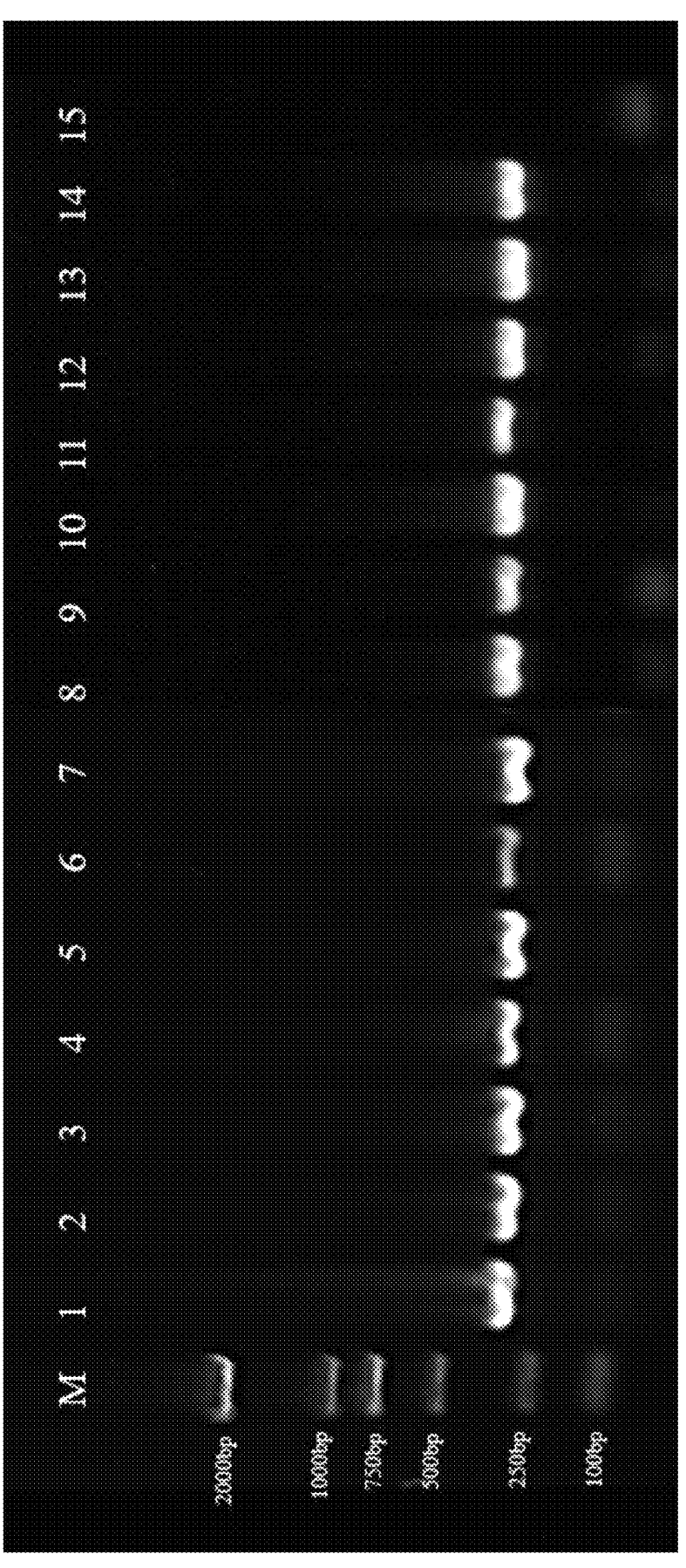
FIG. 4 is an electrophoretogram showing the universality test on 14 geographical populations of Asian gypsy moth distribution in China using primers AGM(F) and AGM(R) in a preferred example of the present disclosure, in which, M refers to DL2000 DNA marker. Lanes 1-15 refer to *Lymantria dispar* collected in Tianjin, Hegang, Qingdao, Chifeng, Chengde, Zhangjiakou, Charisu, Tongliao, Beijing, Dalian, Xianyang, Shuozhou, Yuncheng, and Ulanhot, respectively.

(3) AGM(F), AGM(R) were used to test the universality of different geographical populations of Asian gypsy moth. In addition, 14 geographical populations in China (Table 1) were collected for verification, with water as a blank control. After electrophoresis, it was found that the SS-COI specific primers of *Lymantria dispar* had the ability to amplify 14 geographical populations in China (FIG. 4).

TABLE 1

| Collection places of *Lymantria dispar* and its relatives | | |
| --- | --- | --- |
| Species | Collection place | Collection year |
| Asian gypsy moth | Guizhou | 2021 July |
| | Chengdu | 2021 July |
| | Huder | 2017 July |
| | Xinjiang | 2016 June |
| | Tianjin | 2021 August |
| | Hegang | 2021 August |
| | Qingdao | 2021 July |
| | Chifeng | 2020 July |
| | Chengde | 2018 July |
| | Zhangjiakou | 2018 June |
| | Charisu | 2017 September |
| | Tongliao | 2018 September |
| | Beijing | 2017 September |
| | Dalian | 2021 August |
| | Xianyang | 2020 July |
| | Shuozhou | 2020 August |
| | Yuncheng | 2017 September |

TABLE 1-continued

| Collection places of *Lymantria dispar* and its relatives | | |
|---|---|---|
| Species | Collection place | Collection year |
| | Ulanhot | 2020 August |
| | Japan | 2017 September |
| *Lymantria monacha* | Inner Mongolia | 2017 June |
| *Lymantria xylina* | Fujian | 2020 June |
| *Lymantria apicebrunnea* | Yunnan | 2021 July |

Figure 5:
FIG. 5 is an electrophoretogram showing the universality for detecting AGM(F) and AGM(R) by using tissue DNA of a single Asian gypsy moth at different development stages as templates in a preferred example of the present disclosure, in which M refers to DL2000 DNA marker. Lanes 1-10 each refers to eggs, first instar larva, second instar larva, third instar larva, fourth instar larva, fifth instar larva, sixth instar larva, pupae and adults of Asian gypsy moth, as well as sterile water.

(4) genomic DNA of single egg, first instar larva, second instar larva, third instar larva, fourth instar larva, fifth instar larva, sixth instar larva, pupae and adults of Asian gypsy moth was extracted as a template, and specific primers AGM(F) and AGM(R) were used for PCR amplification detection. According to electrophoresis results, it was showed that target bands of Asian gypsy moth in different instars and different insect states were all amplified by using the pair of primers (FIG. 5).

(5) Sensitivity Test of Asian Gypsy Moth-Specific Primers

Figure 6:
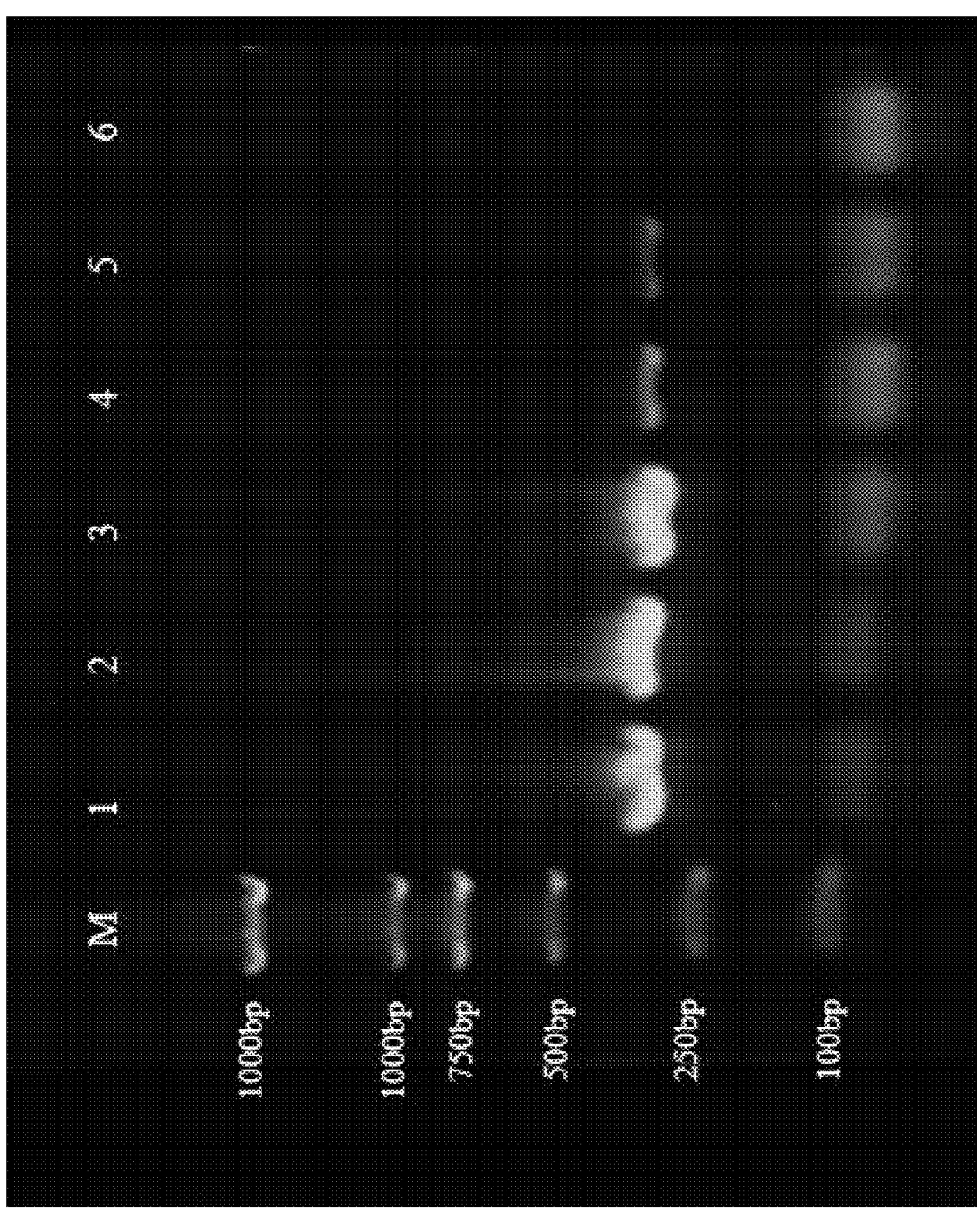
FIG. 6 shows the universality test of AGM(F) and AGM (R) using *Lymantria dispar:Lymantria xylina* in different proportions as templates in a preferred embodiment of the preferred example of the present disclosure, in which M refers to DL2000 DNA marker. Lanes 1-6 each refers to DNA templates of *Lymantria dispar:Lymantria xylina* at 1:0, 1:1, 1:10, 1:50, 1:100 and 1:1000.

The DNA templates of *Lymantria dispar* and *Lymantria xylina* in different ratios of 1:0, 1:1, 1:10, 1:50, 1:100, and 1:1000 were selected to test the sensitivity of the specific primers. The concentrations of *Lymantria dispar* and *Lymantria xylina* standard solutions were 20 ng/μl. Electrophoresis results showed that the target bands appeared in all concentration gradients except for 1:1000 (FIG. 6).

The embodiments of the present disclosure have at least the following advantages:

1. Sampling range is wide. Strictly speaking, Asian gypsy moth is the collective name of *Lymantria dispar asiatica* and *Lymantria dispar japonica*. In previous studies, only a small amount of geographical populations in China were covered. In this study, not only 18 geographical populations widely distributed in China but also *Lymantria dispar japonica* were collected, covering a comprehensive range, making the results more likely to be widely implemented.

2. In the present disclosure, *Lymantria apicebrunnea* are collected, which breaks out and may spread in individual areas of China in the past two years and is not the quarantine moth listed in North America and other countries, so as to prevent it from being mistakenly identified as an Asian gypsy moth during quarantine. The primers designed by the present disclosure are able to distinguish the two species accurately.

3. The primer design of the present disclosure is reliable, and the adopted universal primers are the modified degenerate primers, which may improve the amplification success rate and the amplification effect, providing more reliable sequence information for the design of the specific primers.

4. The technical scheme of the present disclosure has a wide range of application, and each instar and development stage of Asian gypsy moth from egg to adult are detected in the present disclosure, which proves that the primers are capable of detecting each stage of Asian gypsy moth.

5. The PCR system of the present disclosure is simple and convenient. It only needs to add primers and templates for amplification, which greatly optimizes the amplification system, saves time, and reduces pollution.

6. The primers provided by the present disclosure have a wide annealing temperature range, and target species may be accurately detected within the range of 49° C.

to 56° C. without false positives, which solves the problem of high false positiveness caused by only one optimum annealing temperature of existing primers.

7. In the present disclosure, the mixed DNA is proposed for detecting quarantine species considering the situation that multiple moth tissues are mixed together and cannot be identified during the quarantine process. Through detection, Asian gypsy moth templates with low concentration may be detected because the primers of the present disclosure have high enough sensitivity (within the range of Asian gypsy moth DNA:relative species DNA=1:100).

Although the present disclosure has been described in detail above with reference to the general description and specific embodiments, it is obvious to those skill in the art that modifications or improvements may be made thereto without departing from the scope of the present disclosure. Therefore, these modifications or improvements without departing from the spirit of the present disclosure fall within the scope of the present disclosure as claimed.

Sequence Listing Information:

DTD Version: V1_3

File Name: HLP20220400312-Sequence Listing.xml

Software Name: WIPO Sequence

Software Version: 2.0.0

Production Date: 2022 Jul. 5

General Information:

Current application/Applicant file reference: HLP20220400312

Earliest priority application/IP Office: CN

Earliest priority application/Application number: 202111593718.2

Earliest priority application/Filing date: 2021 Dec. 24

Applicant name: Beijing Forestry University

Applicant name/Language: en

Invention title: Specific primers for identifying Asian gypsy moth and method of detection thereby (en)

Sequence Total Quantity: 4

Sequences:

Sequence Number (ID): 1

Length: 25

Molecule Type: DNA

Features Location/Qualifiers:

source, 1 . . . 25

>PCR_primers, fwd_name:AGM_F,fwd_seq:ccttc-tacttttatctttacctgtt,rev_name:AGM_R,rev_seq:at-tgtagcagaggtaa ag >mol_type, other DNA >note, specific primer: AGM_F >organism, synthetic construct Residues:

ccttctactt ttatctttac ctgtt 25

Sequence Number (ID): 2

Length: 18

Molecule Type: DNA

Features Location/Qualifiers:

source, 1 . . . 18

>PCR_primers, fwd_name:AGM_F,fwd_seq:ccttc-tactatatctttacctgtt,rev_name:AGM_R,rev_seq:at-tgtagcagaggtaa ag >mol_type, other DNA >note, specific primer: AGM_R >organism, synthetic construct Residues:
attgtagcag aggtaaag 18
Sequence Number (ID): 3
Length: 21
Molecule Type: DNA
Features Location/Qualifiers:

>standard name, w is a or t
misc_feature, 20
>standard name, n is a, t, g or c
Residues:
ggtaatcaga gtatcgwcgn gg 22
END

```
                        SEQUENCE LISTING

Sequence total quantity: 4
SEQ ID NO: 1           moltype = DNA  length = 25
FEATURE                Location/Qualifiers
source                 1..25
                       mol_type = other DNA
                       organism = synthetic construct
SEQUENCE: 1
ccttctactt ttatctttac ctgtt                                    25

SEQ ID NO: 2           moltype = DNA  length = 18
FEATURE                Location/Qualifiers
source                 1..18
                       mol_type = other DNA
                       organism = synthetic construct
SEQUENCE: 2
attgtagcag aggtaaag                                            18

SEQ ID NO: 3           moltype = DNA  length = 21
FEATURE                Location/Qualifiers
source                 1..21
                       mol_type = other DNA
                       organism = synthetic construct
SEQUENCE: 3
aattggwggw ttyggaaayt g                                        21

SEQ ID NO: 4           moltype = DNA  length = 22
FEATURE                Location/Qualifiers
source                 1..22
                       mol_type = other DNA
                       organism = synthetic construct
SEQUENCE: 4
ggtaatcaga gtatcgwcgn gg                                       22
``` source, 1 . . . 21
>PCR_primers, fwd_name:C1_J1709,fwd_seq:aattggwggwttyggaaaytg,rev_name:C1_N2776,
rev_seq:ggtaatcaga gtatcgwcgngg
>mol_type, other DNA
>note, universal primer sequence:C1_J1709
>organism, synthetic construct
misc_feature, 7
>standard name, w is a or t
misc_feature, 10
>standard name, w is a or t
misc_feature, 13 >note, y is c or t
misc_feature, 19
>note, y is c or t
Residues:
aattggwggw ttyggaaayt g 21 Sequence Number (ID): 4
Length: 22
Molecule Type: DNA
Features Location/Qualifiers:
source, 1 . . . 22 >PCR_primers, fwd_name:C1_J1709,fwd_seq:aat-
tggwggwttyggaaaytg,rev_name:C1_N2776,
rev_seq:ggtaatcaga gtatcgwcgngg
>mol_type, other DNA
>note, universal primer sequence:C1_N2776 >organism, synthetic construct
misc_feature, 17

What is claimed is:

1. A method for detecting Asian gypsy moth, comprising the following steps:

(1) extracting genomic DNA of an insect to be tested;

(2) performing PCR amplification using a pair of specific primers and genomic DNA as a template, wherein the specific primers comprise a forward primer consisting of SEQ ID NO: 1 and a reverse primer consisting of SEQ ID NO:2 and PCR amplification reaction comprises 12.5 μl of 2×PCR premix, 1-2 μl of 10 pmol/μl forward and reverse primers, 1-3 μl of DNA template with a concentration of 20 ng/μl, with a total volume of 25 μl;

wherein the PCR amplification conditions comprise an initial denaturation for 2 min at 94° C.; followed by 30 cycles of denaturation at 94° C. for 30 s, annealing at 49° C. to 56° C. for 30 s, and extension at 72° C. for 1 min; with a final extension at 72° C. for 5 min; and resulting products are stored at 40° C.;

wherein the PCR premix comprises a Taq DNA polymerase, a deoxyribonucleoside triphosphate (dNTP), a magnesium ion, and a reaction buffer; and (3) analyzing amplified products; wherein analyzing is performed by detecting the amplified products by agarose gel electrophoresis, and if a characteristic band of 350 bp appears, determining that the insect detected is Asian gypsy moth.

2. The method according to claim 1, wherein the temperature for the annealing is 50° C.

\* \* \* \* \*